US00PP28675P3

(12) United States Plant Patent
Bergman

(10) Patent No.: US PP28,675 P3
(45) Date of Patent: Nov. 21, 2017

(54) ***CHRYSANTHEMUM* PLANT NAMED 'CIDZ0061'**

(50) Latin Name: *Chrysanthemum×morifolium*
Varietal Denomination: CIDZ0061

(71) Applicant: SYNGENTA PARTICIPATIONS AG, Basel (CH)

(72) Inventor: Wendy R. Bergman, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 64 days.

(21) Appl. No.: 14/756,164

(22) Filed: Aug. 10, 2015

(65) Prior Publication Data

US 2016/0057914 P1 Feb. 25, 2016

Related U.S. Application Data

(60) Provisional application No. 62/039,706, filed on Aug. 20, 2014.

(51) Int. Cl.
*A01H 5/02* (2006.01)

(52) U.S. Cl.
USPC ..... Plt./287

(58) Field of Classification Search
USPC ..... Plt./287
See application file for complete search history.

(56) References Cited

PUBLICATIONS

UPOV hit on *Chrysanthemum* named 'CIDZ0061', CA PBR 13-8100, published Oct. 31, 2013.*

* cited by examiner

*Primary Examiner* — Anne Grunberg
(74) *Attorney, Agent, or Firm* — Dale Skalla

(57) ABSTRACT

A new *Chrysanthemum* plant named 'CIDZ0061' particularly distinguished by the large, golden-bronze, decorative-type inflorescences with a red-bronze center, compact plant habit, excellent plant strength and uniformity, and a flowering response of 8 weeks when cultivated under short-day conditions.

1 Drawing Sheet

Latin name of the genus and species of the plant claimed: *Chrysanthemum×morifolium.*

Varietal denomination: 'CIDZ0061'.

BACKGROUND OF THE NEW PLANT

The present invention comprises a new *Chrysanthemum*, botanically known as *Chrysanthemum×morifolium*, and hereinafter referred to by the variety name 'CIDZ0061'.

'CIDZ0061' is a product of a planned breeding program. The new cultivar has large, golden-bronze, decorative-type inflorescences with a red-bronze center, compact plant habit, excellent plant strength and uniformity, and a flowering response of 8 weeks when cultivated under short-day conditions.

'CIDZ0061' originated from a hybridization made in September 2007 in a greenhouse in Bogota, Columbia. The female parent was the unpatented, proprietary plant designated 'B0858', having pink, decorative-type flowers (inflorescences), a more vigorous growth habit, but smaller sized flowers when compared to 'CIDZ0061'.

The male parent of 'CIDZ0061' was the unpatented, proprietary plant designated as 'B1177', with yellow, decorative-type inflorescences developing more disc florets than inflorescences of 'CIDZ0061'.

The seed was sown in July 2008 and the resulting plants were grown in pots under a shade structure in Fort Myers, Fla. 'CIDZ0061' was selected as one flowering plant within the progeny of the stated cross in December 2008.

The first act of asexual reproduction of 'CIDZ0061' was accomplished when vegetative cuttings were propagated from the initial selection in March 2009 in Fort Myers, Fla.

BRIEF SUMMARY OF INVENTION

Horticultural examination of plants grown from cuttings of the plant initiated in August 2009, and continuing thereafter, has demonstrated that the combination of characteristics as herein disclosed for 'CIDZ0061' are firmly fixed and are retained through successive generations of asexual reproduction.

'CIDZ0061' has not been observed under all possible environmental conditions. The phenotype may vary significantly with variations in environment such as temperature, light intensity, and day length.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIDZ0061' with colors being as true as possible with an illustration of this type. The photographic drawings show in FIG. 1 a close-up of the inflorescences and in FIG. 2, a flowering plant of the new variety.

DETAILED BOTANICAL DESCRIPTION

The plant descriptions and measurements were taken indoors in Nipomo, Calif., on Aug. 14, 2014 on about 11 week old plants. Unrooted cuttings had been planted, 4 plants per pot, in 6 inch pots on May 24, 2014. The plants were pinched and moved to short days on Jun. 16, 2014 to induce flowering.

Figure 1:
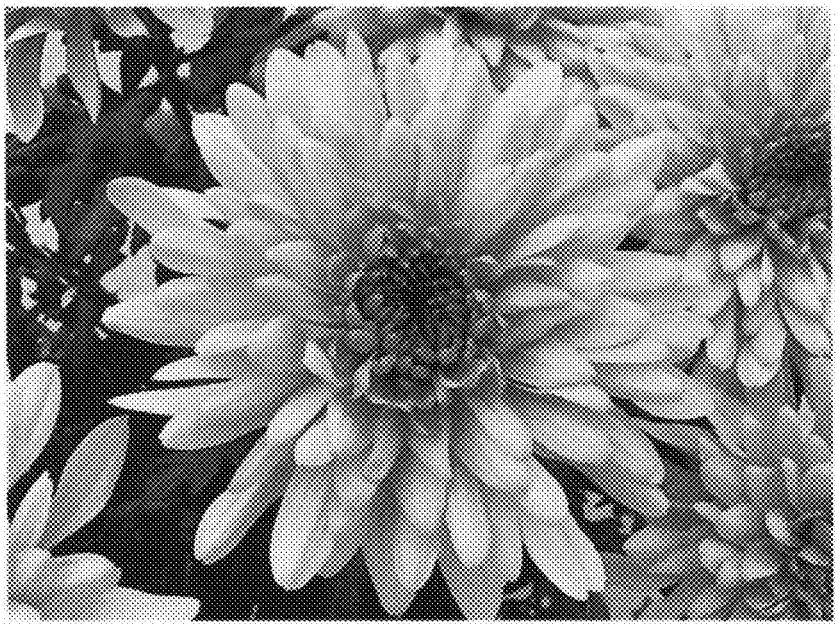
Figure 2:
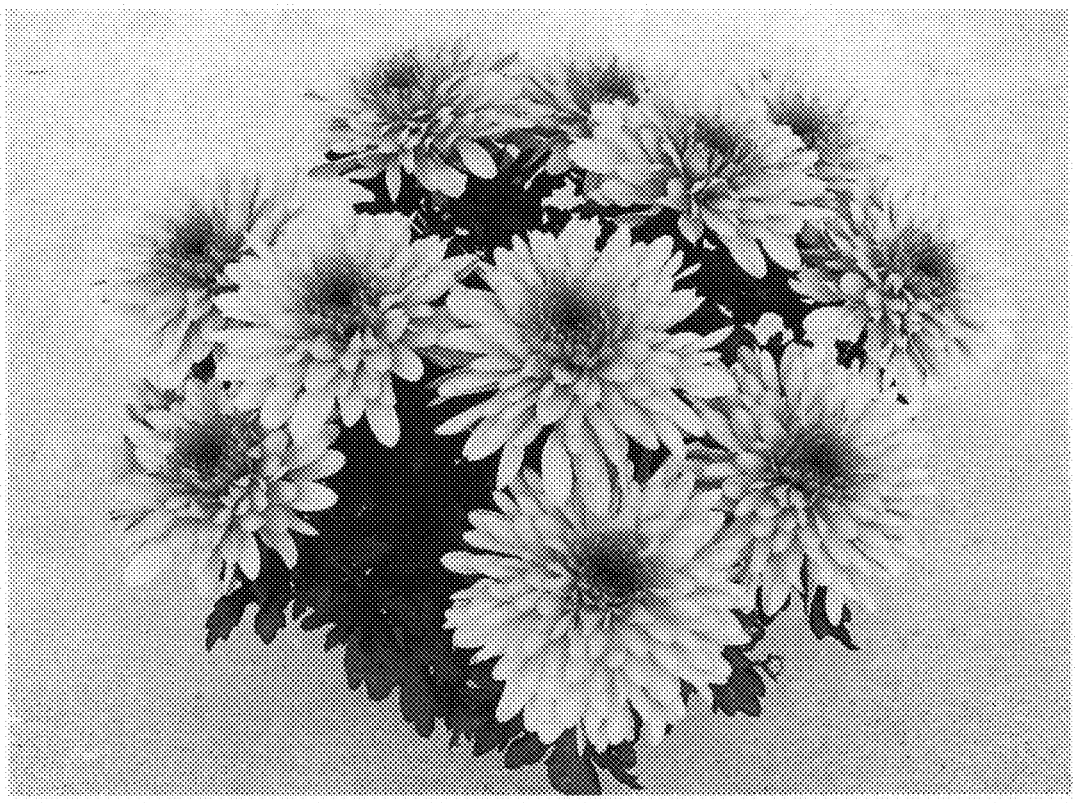

The aforementioned photographs: FIGS. 1 and 2 were taken in Nipomo, Calif. in May 2013, and showing a plant from a trial, in which flowering had been induced by applying black cloth. These plants were about 11 weeks of age. Unrooted cuttings had been planted, 4 plants per pot, in 6 inch pots. The terminal buds were removed leaving the lateral buds to mature, approximately 3 weeks prior to flowering.

Color references are made to The Royal Horticultural Society Colour Chart (R.H.S.) 2001.

TABLE 1

DIFFERENCES BETWEEN THE NEW VARIETY 'CIDZ0061' AND A MOST SIMILAR VARIETY

| | 'CIDZ0061' | 'YOGRAND RAPIDS', U.S. Pat. No. PP22,178 |
|---|---|---|
| Growth habit: | Shorter and more compact | More vigorous growth |
| Plant habit: | More spreading | More upright directed |
| Flower size: | Larger | Smaller |

Plant:

*Form, growth and habit.*—Herbaceous pot-type, stems upright, freely branching, strong and moderately vigorous growth habit.

*Plant height.*—22.0-25.0 cm.

*Plant height (inflorescence included).*—27.0-30.0 cm.

*Plant width.*—31.0-34.0 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 141A.

*Lower surface.*—Closest to 138B.

*Mature, leaf color, upper surface.*—Closest to RHS 137B.

*Lower surface.*—Closest to RHS 138A.

*Length.*—7.5-8.8 cm.

*Width.*—7.0-9.0 cm.

*Shape.*—Ovate.

*Base shape.*—Attenuate.

*Apex shape.*—Mucronulate.

*Margin.*—Palmately lobed; irregularly incised, somewhat serrate.

*Texture, upper surface.*—Bifid T-shaped hairs.

*Lower surface.*—Bifid T-shaped hairs.

*Color of veins, upper surface.*—RHS 147D becoming indistinct.

*Color of veins, lower surface.*—RHS 147C.

*Pattern of veining.*—Palmate.

*Petiole color.*—RHS 137B.

*Length.*—1.5-2.3 cm.

*Diameter.*—0.4-0.6 cm.

*Texture.*—Bifid T-shaped hairs.

Stem:

*Quantity of main branches per plant.*—3-4.

*Color of stem.*—RHS 139D.

*Length of stem.*—About 16-20 cm.

*Diameter.*—0.4-0.7 cm.

*Length of internodes.*—1.3-3.3 cm.

*Texture.*—Bifid T-shaped hairs.

*Color of peduncle.*—RHS 147C.

*Length of peduncle.*—2.0-5.25 cm.

*Peduncle diameter.*—0.2-0.3 cm.

*Texture.*—Bifid T-shaped hairs.

Inflorescence:

*Type.*—Compositae type, decorative-type inflorescences borne terminally above foliage, ray florets arranged acropetally on a capitulum.

*Quantity of short days to flowering (response time).*—8 weeks.

*Natural season flowering.*—Not determined on this variety.

*Quantity of inflorescences per plant.*—52-60.

*Lastingness of individual blooms on the plant.*—4 weeks.

*Fragrance.*—Slightly spicy.

Bud (just when opening/showing color):

*Color.*—Closest to RHS 172B.

*Length.*—1.5-1.8 cm.

*Width.*—1.6 cm.

*Shape.*—Oblate.

Immature inflorescence:

*Diameter.*—5.5-7.0 cm.

*Color of ray florets, upper surface.*—Closest to 16A overlain with 163A near the center and 13A overlain with 163B on the outer portion.

*Lower surface.*—Closest to RHS 181A.

Mature inflorescence:

*Diameter.*—8.0-9.5.0 cm.

*Depth.*—2.5-3.25 cm.

*Total diameter of disc.*—Not present.

*Receptacle color.*—RHS 145B.

*Receptacle height.*—0.4 cm.

*Receptacle diameter.*—0.6-0.8 cm.

Ray florets:

*Average quantity of florets.*—250-290.

*Color of florets, upper surface.*—Closest to RHS 12A overlain with 167C.

*Lower surface.*—Closest to RHS 163C overlain with 180A.

*Length.*—3.0-4.5 cm.

*Width.*—0.9-1.2 cm.

*Shape.*—Elliptical.

*Apex shape.*—Retuse.

*Margin.*—Entire.

*Texture, upper surface.*—Papillose.

*Lower surface.*—Papillose.

Disc florets:

*Average quantity of florets.*—None present.

Phyllaries:

*Quantity.*—About 27.

*Color, upper surface.*—RHS 138A.

*Lower surface.*—RHS 147B.

*Length.*—0.6-0.9 cm.

*Width.*—0.15-0.2 cm.

*Shape.*—Lanceolate.

*Apex shape.*—Acute.

*Base.*—Fused.

*Margins.*—Entire; slightly papery.
*Texture, upper surface.*—Glabrous.
*Lower surface.*—Bifid T-shaped hairs.

Reproductive organs:

*Pistil.*—1.
*Length.*—0.6 cm.
*Style color.*—RHS 155C.
*Style length.*—0.45 cm.
*Stigma color.*—RHS 17C.
*Stigma shape.*—Bi-parted.
*Ovary color.*—RHS 155C but more translucent.
*Stamens*.—None present.
*Color of filaments.*—RHS 155C.
*Length filaments.*—0.4-0.5 cm.
*Anther color.*—RHS 15A.
*Anther length.*—0.15 cm.
*Anther shape.*—Oval.
*Pollen amount.*—Absent.
*Fertility/seed set.*—Has not been observed to date.
*Disease/pest resistance.*—Has not been observed to date.

What is claimed is:

1. A new and distinct variety of *Chrysanthemum* plant named 'CIDZ0061' substantially as illustrated and described herein.

* * * * *